US012678138B2

(12) United States Patent
Schröcker et al.

(10) Patent No.: US 12,678,138 B2

(45) Date of Patent: Jul. 14, 2026

(54) METHOD AND SYSTEM FOR ENHANCED VISUALIZATION OF BLOOD FLOW ULTRASOUND IMAGING WITH GLYPHS

(71) Applicant: GE Precision Healthcare LLC, Waukesha, WI (US)

(72) Inventors: Gerald Schröcker, Salzburg (AT); Daniel Buckton, Salzburg (AT)

(73) Assignee: GE Precision Healthcare LLC, Waukesha, WI (US)

( * ) Notice: Subject to any disclaimer, the term of this patent is extended or adjusted under 35 U.S.C. 154(b) by 116 days.

(21) Appl. No.: 18/670,217

(22) Filed: May 21, 2024

(65) Prior Publication Data

US 2025/0359849 A1 Nov. 27, 2025

(51) Int. Cl.
A61B 8/00 (2006.01)
A61B 8/06 (2006.01)

(52) U.S. Cl.
CPC ............... A61B 8/463 (2013.01); A61B 8/06 (2013.01); A61B 8/488 (2013.01)

(58) Field of Classification Search
CPC ............ A61B 8/463; A61B 8/06; A61B 8/488
See application file for complete search history.

(56) References Cited

U.S. PATENT DOCUMENTS

| | | | |
|---|---|---|---|
| 8,761,474 B2 | 6/2014 | Yu et al. | |
| 8,911,373 B2 | 12/2014 | Haugaard et al. | |
| 11,154,272 B2 | 10/2021 | Yu et al. | |
| 11,701,081 B2 | 7/2023 | Wang et al. | |
| 11,771,396 B2 | 10/2023 | Kapoor et al. | |
| 2008/0015440 A1* | 1/2008 | Shandas | A61B 8/13 |
| | | | 600/458 |
| 2012/0038662 A1* | 2/2012 | Dicklin | G09G 5/377 |
| | | | 345/635 |
| 2019/0117195 A1 | 4/2019 | Miles et al. | |

OTHER PUBLICATIONS

Jensen et al. Ultrasound Vector Flow Imaging—Part I: Sequential Systems, IEEE Transactions on Ultrasonics, Ferroelectrics, and Frequency Control, vol. 63, No. 11, Nov. 2016, 1704-1721.*

* cited by examiner

*Primary Examiner* — Bo Joseph Peng

(74) *Attorney, Agent, or Firm* — McAndrews, Held & Malloy, Ltd.; Daniel Bissing; David Bates

(57) ABSTRACT

Systems and methods for enhancing visualization of blood flow ultrasound imaging with glyphs presented in a hexagonal packing arrangement are provided. The method includes transmitting, by an ultrasound probe, ultrasound beams into a region of interest. The method includes converting, by the ultrasound probe, received echoes to generate ultrasound signals corresponding to the ultrasound beams. The method includes processing, by a receive beamformer, the ultrasound signals to generate beamformed signals. The method includes processing, by at least one processor, the beamformed signals to generate an ultrasound image. The method includes processing, by the at least one processor, the beamformed signals to generate velocity information of the region of interest. The method includes causing, by the at least one processor, a display system to present the ultrasound image overlaid with glyphs generated from the velocity information of the region of interest. The glyphs are presented in a hexagonal packing arrangement.

16 Claims, 10 Drawing Sheets

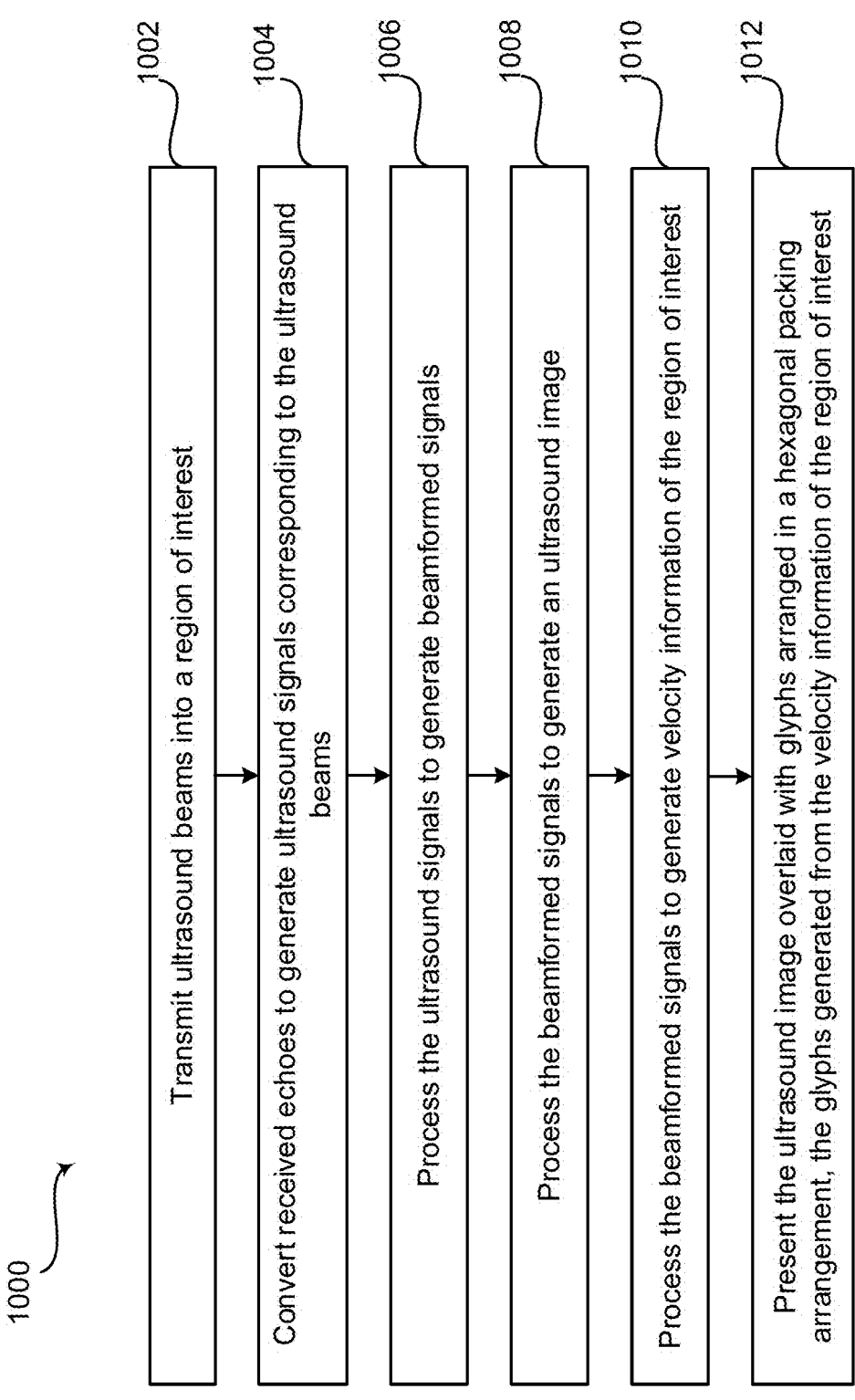

1000

1002 Transmit ultrasound beams into a region of interest

1004 Convert received echoes to generate ultrasound signals corresponding to the ultrasound beams 1006 Process the ultrasound signals to generate beamformed signals 1008 Process the beamformed signals to generate an ultrasound image 1010 Process the beamformed signals to generate velocity information of the region of interest 1012 Present the ultrasound image overlaid with glyphs arranged in a hexagonal packing arrangement, the glyphs generated from the velocity information of the region of interest

FIG. 10

METHOD AND SYSTEM FOR ENHANCED VISUALIZATION OF BLOOD FLOW ULTRASOUND IMAGING WITH GLYPHS

Certain embodiments relate to ultrasound imaging. More specifically, certain embodiments relate to a method and system for enhancing visualization of blood flow ultrasound imaging with glyphs presented in a hexagonal packing arrangement.

BACKGROUND

Ultrasound imaging is a medical imaging technique for imaging organs and soft tissues in a human body. Ultrasound imaging uses real time, non-invasive high frequency sound waves to produce a series of two-dimensional (2D), three-dimensional (3D), and/or four-dimensional (4D) images.

Ultrasound imaging is an important diagnostic tool in assessing the cardiovascular system. For example, the distribution of blood velocities within a blood vessel provides valuable diagnostic information. Visualization of blood flow information may be provided by acquiring ultrasound image data in a region of interest having blood flow, analyzing the ultrasound image data to estimate a blood velocity vector field having information regarding a magnitude and orientation of the blood flow, and displaying graphical elements providing visual information regarding the magnitude and orientation of the blood flow. The blood velocity vector field may be estimated by blood speckle tracking, directional cross-correlation analysis, phase shift estimation, Doppler analysis, and/or any suitable flow vector estimation method. Graphical elements, such as arrows, may be overlaid in a grid on an ultrasound image, where the orientation of each arrow in the grid corresponds with a flow direction, and a size of the arrow corresponds with a flow magnitude. However, the arrows or other graphical elements (referred to herein as glyphs) overlaid on the ultrasound image may not provide a desirable amount of data points. Moreover, the glyphs may be difficult to visualize, particularly for slower moving flows.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for enhancing visualization of blood flow ultrasound imaging with glyphs presented in a hexagonal packing arrangement, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

BRIEF DESCRIPTION OF SEVERAL VIEWS OF THE DRAWINGS

FIG. 10 is a flow chart illustrating exemplary steps that may be utilized for enhancing visualization of blood flow ultrasound imaging with glyphs presented in a hexagonal packing arrangement, in accordance with various embodiments.

DETAILED DESCRIPTION

Figure 1:
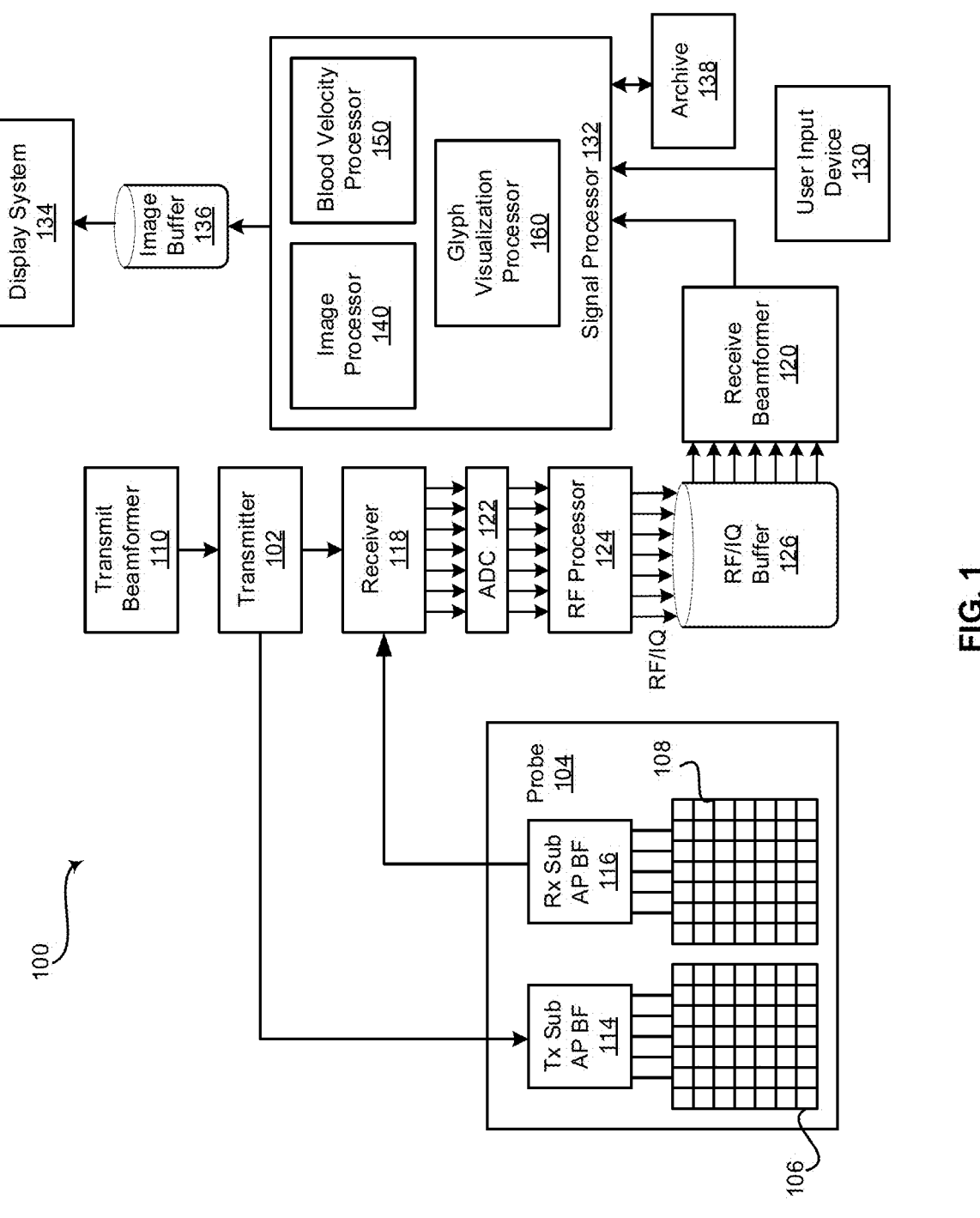
FIG. 1 is a block diagram of an exemplary ultrasound system that is operable to enhance visualization of blood flow ultrasound imaging with glyphs presented in a hexagonal packing arrangement, in accordance with various embodiments.

Certain embodiments may be found in a method and system for enhancing visualization of blood flow ultrasound imaging with glyphs presented in a hexagonal packing arrangement. For example, aspects of the present disclosure have the technical effect of densely covering a blood vessel area to provide a heightened understanding of small flow features, such as turbulence, by positioning the glyphs in a tightest possible packing arrangement, which is hexagonal packing. Moreover, aspects of the present disclosure have the technical effect of enhancing visualization of blood flows having lower velocities by dynamically compressing the velocity magnitude using a non-linear function to enlarge glyphs representing the lower velocity blood flows.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general-purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized, and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising", "including", or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode, which can be one-dimensional (1D), two-dimensional (2D), three-dimensional (3D), or four-dimensional (4D), and comprising Brightness mode (B-mode or 2D mode), Motion mode (M-mode), Color Motion mode (CM-mode), Color Flow mode (CF-mode), Pulsed Wave (PW) Doppler, Continuous Wave (CW) Doppler, Contrast Enhanced Ultrasound (CEUS), and/or sub-modes of B-mode and/or CF-mode such as Harmonic Imaging, Shear Wave Elasticity Imaging (SWEI), Strain Elastography, Tissue Velocity Imaging (TVI), Power Doppler Imaging (PDI), B-Flow Color (BFC), Micro Vascular Imaging (MVI), Ultrasound-Guided Attenuation Parameter (UGAP), and the like.

Furthermore, the term processor or processing unit, as used herein, refers to any type of processing unit that can carry out the required calculations needed for the various embodiments, such as single or multi-core Central Processing Unit (CPU), Accelerated Processing Unit (APU), Graphics Processing Unit (GPU), Digital Signal Processor (DSP), Field Programmable Gate Array (FPGA), System on a Chip (SoC), Application-Specific Integrated Circuit (ASIC), or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

FIG. 1 is a block diagram of an exemplary ultrasound system 100 that is operable to enhance visualization of blood flow ultrasound imaging with glyphs presented in a hexagonal packing arrangement, in accordance with various embodiments. Referring to FIG. 1, there is shown an ultrasound system 100. The ultrasound system 100 comprises a transmitter 102, an ultrasound probe 104, a transmit beamformer 110, a receiver 118, a receive beamformer 120, A/D converters 122, a RF processor 124, a RF/IQ buffer 126, a user input device 130, a signal processor 132, an image buffer 136, a display system 134, and an archive 138. The ultrasound system 100 may be a standard console, a miniaturized ultrasound system, wired or wireless ultrasound system, and/or any ultrasound system capable of transmitting and receiving acoustic energy from a plurality of transducer elements and at a plurality of directions. In certain embodiments, the transmitter 102 and/or transmit beamformer 110 may embedded in the ultrasound probe 104.

The transmitter 102 may comprise suitable logic, circuitry, interfaces and/or code that may be operable to drive an ultrasound probe 104. The transmitter 102 may be configured to receive transmit settings for driving the ultrasound probe 104 from the signal processor 132. For example, the transmitter 102 may receive transmit settings such as a transmit frequency, waveform shape, bandwidth, and/or any suitable transmit settings from the signal processor 132. The ultrasound probe 104 may be a phased array, linear array, curved array, or any suitable shape or combination of shapes. The ultrasound probe 104 may comprise an array of transducer elements, such as piezoelectric elements, micromachined elements, piezoelectric micromachined ultrasound transducers (PMUT) elements, capacitive micromachined ultrasound transducers (CMUT) elements, and/or any suitable transducer elements capable of converting control signals to acoustic energy and converting acoustic energy to ultrasound signals. The ultrasound probe 104 may comprise a group of transmit transducer elements 106 and a group of receive transducer elements 108, that normally constitute the same elements. The group of transmit transducer elements 106 may emit ultrasonic signals through oil and a probe cap and into a target. In a representative embodiment, the ultrasound probe 104 may be operable to acquire ultrasound image data covering at least a substantial portion of an anatomy, such as a heart, fetus, blood vessels, pelvic region, or any suitable anatomical region.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals (i.e., transmit beams) into a region of interest (e.g., human, animal, underground cavity, physical structure and the like). In various embodiments, the transmit sub-aperture beamformer 114 may not be included. The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, which undergo sub-aperture beamforming by a receive sub-aperture beamformer 116 and are then communicated to a receiver 118. In various embodiments, the receive sub-aperture beamformer 116 may not be included. The receiver 118 may comprise suitable logic, circuitry, interfaces and/or code that may be operable to receive the signals from the receive sub-aperture beamformer 116 and/or receive transducer elements 108. The analog signals may be communicated to one or more of the plurality of A/D converters 122.

The ultrasound system 100 may further include a matching layer (not shown) having an acoustic impedance. Exemplary matching layer embodiments are disclosed in U.S. Pat. No. 7,757,389, filed on Jun. 25, 2007, the entirety of which is incorporated by reference herein. The matching layer may be positioned or located such that it is between the patient and the transducer elements 106, 108. The matching layer is configured to have an acoustic impedance between an impedance of a blood flow or tissue of the anatomical region and an impedance of the material of the transducer elements 106, 108. The matching layer is configured to absorb waves reflected from the anatomical region due to the difference of the acoustic impedance between the anatomy at the region of interest and the impedance of the transducer elements 106, 108.

The ultrasound system 100 may further include a damping block (not shown) configured to absorb ultrasound energy. The damping block may be positioned behind the some or all of transducer elements 106, 108. Exemplary damping block embodiments are disclosed by "acoustic backing material 204" in U.S. Pat. No. 11,378,554, filed on Sep. 27, 2019, the entirety of which is incorporated by reference herein. The damping block may include various components with acoustic-dampening properties, such that at least a portion reflected ultrasonic waves received at the ultrasound system 100 are absorbed and not reflected back towards the patient by the ultrasound system 100. For example, the damping block may comprise a solidified blend of a backing polymer matrix, filler particles, and one or more additives (e.g., hardeners, crosslinkers), where the backing polymer matrix may be formed from a thermoplastic, thermosetting polymer precursors, or a resin, which may be selected in part for the acoustic-dampening properties thereof.

The plurality of A/D converters 122 may comprise suitable logic, circuitry, interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118 or in the probe 104.

The RF processor 124 may comprise suitable logic, circuitry, interfaces and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The receive beamformer 120 may comprise suitable logic, circuitry, interfaces and/or code that may be operable to perform digital beamforming processing to, for example, sum the delayed channel signals received from RF processor 124 via the RF/IQ buffer 126 and output a beam summed signal. The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital. In various embodiments, the ultrasound system 100 comprises a plurality of receive beamformers 120.

The user input device 130 may be utilized to input patient data, scan parameters, settings, select protocols and/or templates, select and/or modify a region of interest, and the like. In an exemplary embodiment, the user input device 130 may be operable to configure, manage and/or control operation of one or more components and/or modules in the ultrasound system 100. In this regard, the user input device 130 may be operable to configure, manage and/or control operation of the transmitter 102, the ultrasound probe 104, the transmit beamformer 110, the receiver 118, the receive beamformer 120, the RF processor 124, the RF/IQ buffer 126, the signal processor 132, the image buffer 136, the display system 134, and/or the archive 138. The user input device 130 may include button(s), rotary encoder(s), a touchscreen, motion tracking, voice recognition, a mousing device, keyboard, camera and/or any other device capable of receiving a user directive. In certain embodiments, one or more of the user input devices 130 may be integrated into other components, such as the display system 134 or the ultrasound probe 104, for example. As an example, the user input device 130 may include a touchscreen display.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), or any suitable device for storing images and related information.

The signal processor 132 may be one or more processing units, microprocessors, microcontrollers, Graphics Processing Units (GPUs), and/or the like. The signal processor 132 may be an integrated component, or may be distributed across various locations, for example. In an exemplary embodiment, the signal processor 132 may comprise an image processor 140, a blood velocity processor 150, and a glyph visualization processor 160. The signal processor 132 may be capable of receiving input information from a user input device 130 and/or archive 138, generating an output displayable by a display system 134, and manipulating the output in response to input information from a user input device 130, among other things. The signal processor 132, image processor 140, blood velocity processor 150, and glyph visualization processor 160 may be capable of executing any of the method(s) and/or set(s) of instructions discussed herein in accordance with the various embodiments, for example.

The ultrasound system 100 may be operable to continuously acquire ultrasound scan data at a frame rate that is suitable for the imaging situation in question. Typical frame rates range from 20-120 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes' worth of frames of ultrasound scan data but it can also store less. The frames of ultrasound scan data are stored in a manner to facilitate retrieval thereof according to its order or time of acquisition. The image buffer 136 may be embodied as any known data storage medium.

The signal processor 132 may include an image processor 140 that comprises suitable logic, circuitry, interfaces and/or code that may be operable to process beamformed signals received from the receive beamformer 120 and/or any suitable ultrasound image data to generate ultrasound images. For example, the image processor 140 of the signal processor 132 may receive the beamformed signals output from the receive beamformer 120. The image processor 140 may be configured to process ultrasound scan data for generating ultrasound images for presentation on a display system 134. The image processor 140 is operable to perform one or more processing operations according to a plurality of selectable ultrasound modalities on the beamformed signals. As an example, the signal processor 132 may be operable to process the beamformed signals to generate B-mode images, color flow Doppler information, and/or any suitable ultrasound image information. In an exemplary embodiment, the signal processor 132 may be operable to perform display processing and/or control processing, among other things. In an exemplary embodiment, the image processor 140 may be configured to superimpose color flow Doppler information on the generated B-mode images. The generated B-mode images with or without the color flow Doppler information may be presented at the display system 134 and/or stored at archive 138 and/or any suitable data storage medium.

The signal processor 132 may include a blood velocity processor 150 that comprises suitable logic, circuitry, interfaces and/or code that may be operable to analyze the beamformed signals provided by the receive beamformer 120 to generate velocity information of a region of interest, such as blood flow in blood vessels and/or any suitable region of interest. For example, the blood velocity process 150 may be operable to analyze the ultrasound image data to estimate a blood velocity vector field having information regarding a magnitude and orientation of the blood flow. The blood velocity vector field may be estimated by blood speckle tracking, directional cross-correlation analysis, phase shift estimation, Doppler analysis, and/or any suitable flow vector estimation method. As an example, the blood velocity processor 150 may perform blood flow estimation over the region of interest to obtain axial and lateral velocity information of a velocity vector at any given position within the region of interest, such as using synthetic aperture imaging, a transverse oscillation approach, or any suitable approach. The blood velocity processor 150 may be configured to determine the magnitude and orientation of the blood velocity at any given point in the region of interest from the axial and lateral velocity estimates. Accordingly, the blood velocity processor 150 may be configured to generate a blood velocity vector field having information regarding a magnitude and orientation of the blood flow at any given point in the region of interest. The blood velocity vector field may be provided to the glyph visualization processor 160 and/or stored at archive 138 and/or any suitable data storage medium.

The signal processor 132 may include a glyph visualization processor 160 that comprises suitable logic, circuitry, interfaces and/or code that may be operable to generate glyphs from the velocity information received from the blood velocity processor 150 and/or retrieved from the archive and/or any suitable data storage medium. The glyphs are graphical elements configured to provide visualization of a magnitude and orientation of blood flow at any point in the region of interest. For example, the glyphs may be arrows, drops, and/or any suitable shape, icon, and the like capable of providing magnitude and orientation blood velocity information. As an example, an arrow glyph may point in a direction corresponding with an orientation of the blood flow and may be sized to correspond with the magnitude of the blood flow. As another example, a drop glyph may have a thicker head portion (opposite the thin tail portion) pointing in a direction corresponding with an orientation of the blood flow and may be sized to correspond with the magnitude of the blood flow. The glyph visualization processor 160 may comprise suitable logic, circuitry, interfaces and/or code that may be operable to superimpose glyphs arranged in a hexagonal packing arrangement on the ultrasound images generated by the image processor 140. The hexagonal packing arrangement is the densest packing arrangement. Accordingly, visualization of the blood velocity information is enhanced due to the glyphs in the hexagonal packing arrangement densely covering a blood vessel area to provide a heightened understanding of small flow features, such as turbulence. The glyph visualization processor 160 may be configured to overlay the glyphs in the hexagonal packing arrangement directly on an ultrasound image in the region of interest. Alternatively, the glyph visualization processor 160 may be configured to overlay the glyphs in the hexagonal packing arrangement on color flow Doppler information superimposed on the ultrasound image in the region of interest.

Figure 2:
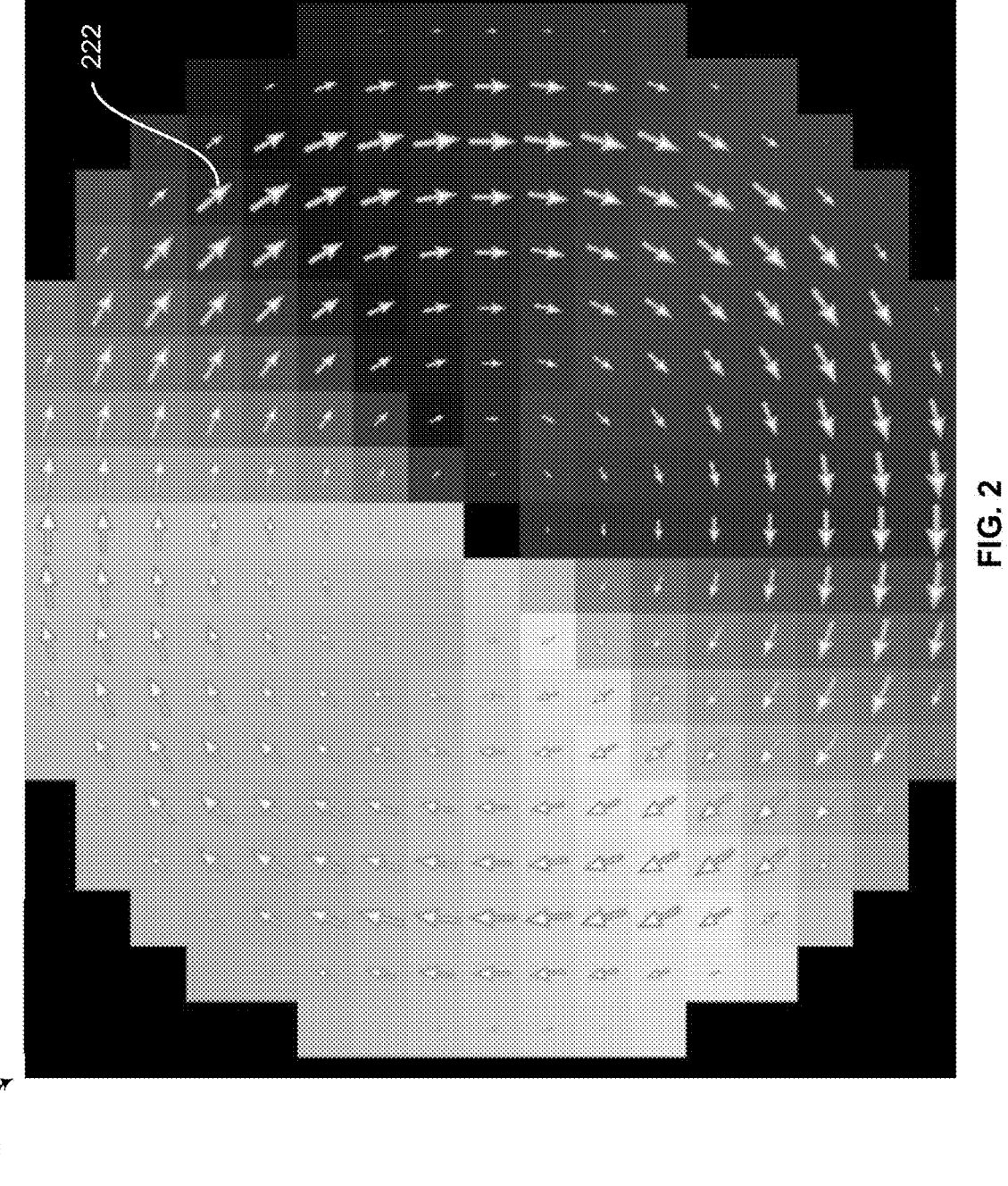
FIG. 2 is an exemplary display of glyphs in a grid layout, in accordance with various embodiments.

FIG. 2 is an exemplary display 200 of glyphs 222 in a grid layout, in accordance with various embodiments. Referring to FIG. 2, a display 200 of glyphs 222 is shown in a grid layout. The glyphs 222 illustrated in FIG. 2 are arrows. The arrow glyphs 222 may provide orientation information of blood flow based on the direction the arrow glyph 222 is pointing. The arrow glyphs 222 may provide magnitude information of blood flow based on a size of each of the arrow glyphs 222. For example, faster velocities may be shown as larger arrow glyphs 222 and slower velocities may be shown as smaller arrow glyphs 222. As shown in FIG. 2, the grid layout provides the glyphs 222 aligned both vertically and horizontally in rows and columns.

Figure 3:
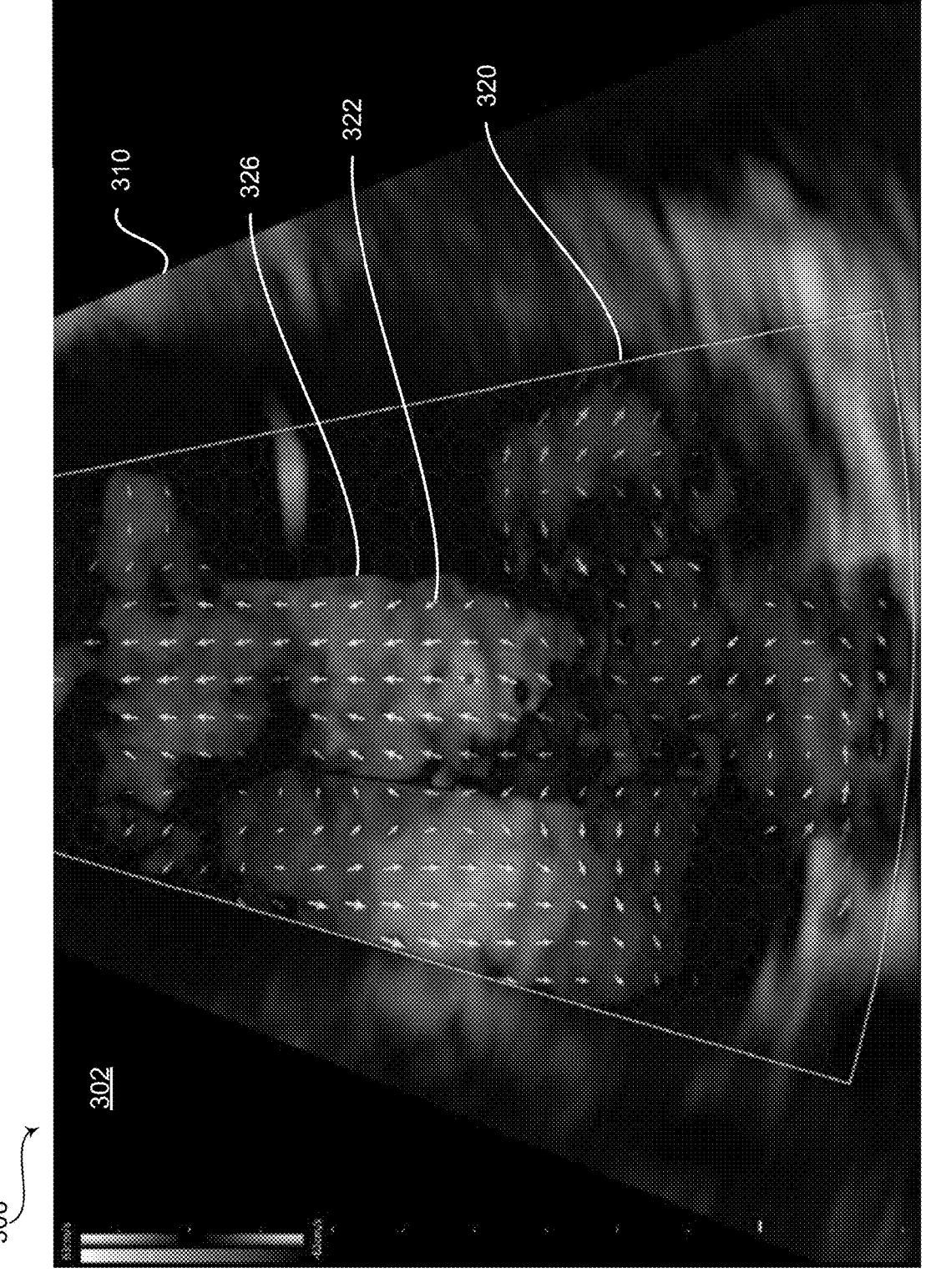
FIG. 3 is an exemplary display of glyphs in a grid layout overlaid on an ultrasound image, in accordance with various embodiments.

FIG. 3 is an exemplary display 300 of glyphs 322 in a grid layout overlaid on an ultrasound image 310, in accordance with various embodiments. Referring to FIG. 3, a display 300 includes an ultrasound image display portion 302 presenting an ultrasound image 310. The ultrasound image 310 includes a region of interest 320 that may include blood vessels having blood flow, for example. The ultrasound image 310 is overlaid with color flow Doppler information 326. The ultrasound image 310 and color flow Doppler information 326 is overlaid with glyphs 322 in a grid layout. The glyphs 322 illustrated in FIG. 3 are arrows. The arrow glyphs 322 may provide orientation information of blood flow based on the direction the arrow glyph 322 is pointing. The arrow glyphs 322 may provide magnitude information of blood flow based on a size of each of the arrow glyphs 322. For example, faster velocities may be shown as larger arrow glyphs 322 and slower velocities may be shown as smaller arrow glyphs 322. As shown in FIG. 3, the grid layout provides the glyphs 322 aligned both vertically and horizontally in rows and columns.

Figure 4:
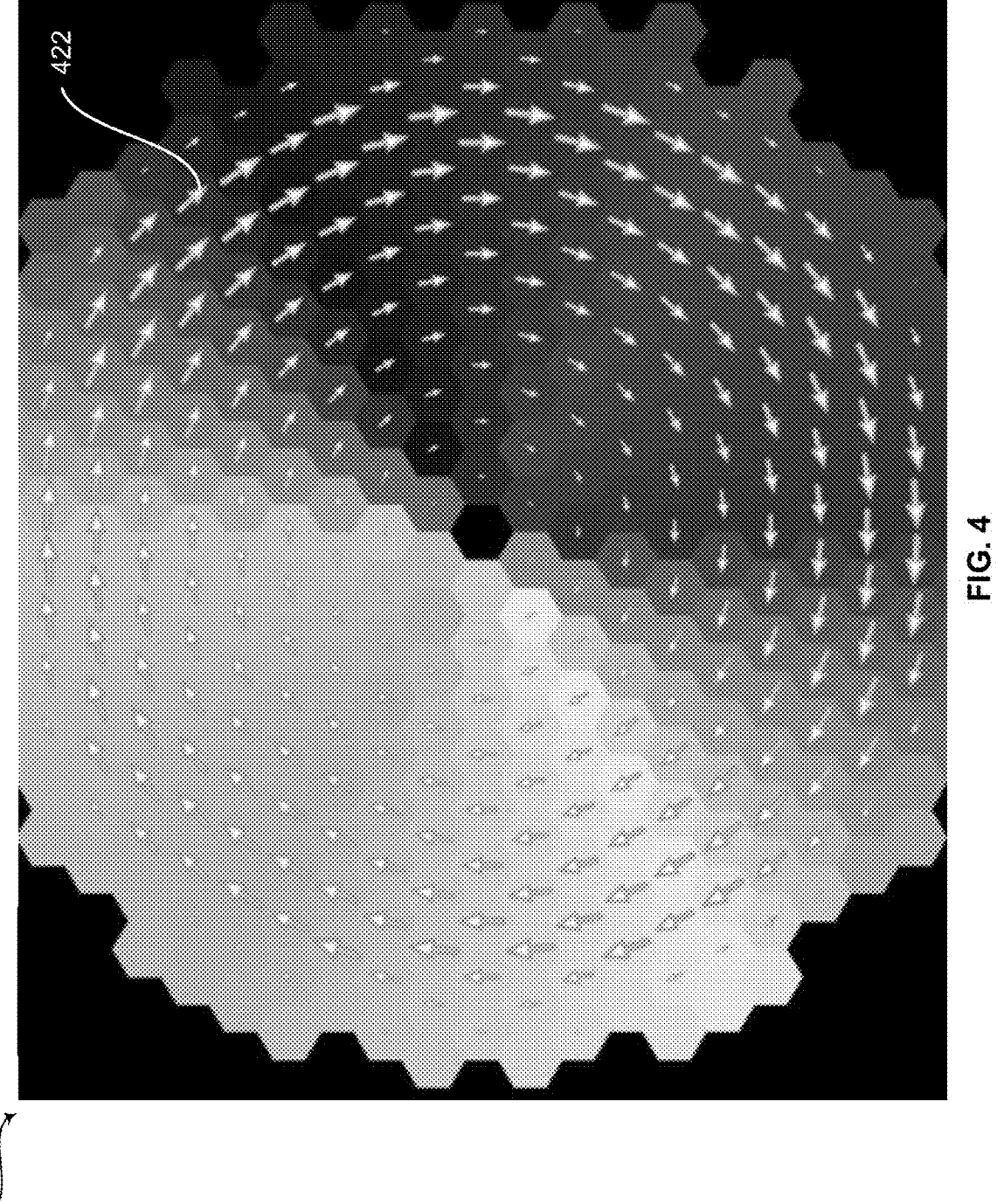
FIG. 4 is an exemplary display of glyphs in a hexagonal packing arrangement, in accordance with various embodiments.

FIG. 4 is an exemplary display 400 of glyphs 422 in a hexagonal packing arrangement, in accordance with various embodiments. Referring to FIG. 4, a display 400 of glyphs 422 is shown in a hexagonal packing arrangement. The glyphs 422 illustrated in FIG. 4 are arrows. The arrow glyphs 422 may provide orientation information of blood flow based on the direction the arrow glyph 422 is pointing. The arrow glyphs 422 may provide magnitude information of blood flow based on a size of each of the arrow glyphs 422. For example, faster velocities may be shown as larger arrow glyphs 422 and slower velocities may be shown as smaller arrow glyphs 422. As shown in FIG. 4, the hexagonal packing arrangement provides vertically overlapping rows of glyphs 422 laterally offset from adjacent rows to provide a densest packing arrangement. By providing the glyphs 422 in the hexagonal packing arrangement, visualization of the blood velocity information is enhanced due to the glyphs 422 densely filling the display 400 to provide a heightened understanding of small flow features, such as turbulence. For example, referring to FIGS. 2 and 4, the hexagonal packing arrangement of the glyphs 422 in FIG. 4 more densely covers the display 400 to provide more velocity information than the glyphs 222 of FIG. 2 arranged in the grid layout.

Figure 5:
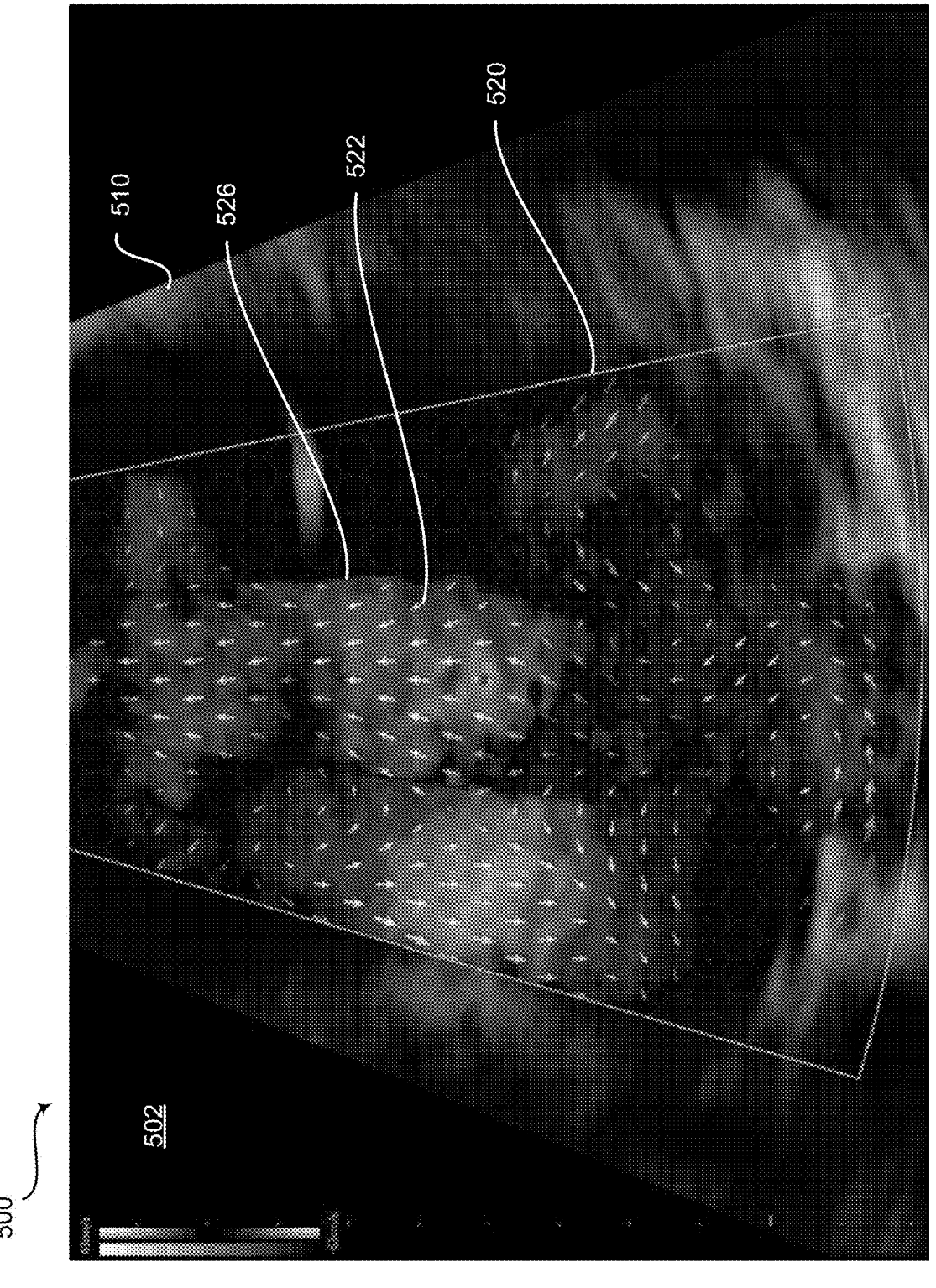
FIG. 5 is an exemplary display of glyphs in a hexagonal packing arrangement overlaid on an ultrasound image, in accordance with various embodiments.

FIG. 5 is an exemplary display of glyphs in a hexagonal packing arrangement overlaid on an ultrasound image, in accordance with various embodiments. Referring to FIG. 5, a display 500 includes an ultrasound image display portion 502 presenting an ultrasound image 510. The ultrasound image 510 includes a region of interest 520 that may include blood vessels having blood flow, for example. The ultrasound image 510 is overlaid with color flow Doppler information 526. The ultrasound image 510 and color flow Doppler information 526 is overlaid with glyphs 522 in a hexagonal packing arrangement. The glyphs 522 illustrated in FIG. 5 are arrows. The arrow glyphs 522 may provide orientation information of blood flow based on the direction the arrow glyph 522 is pointing. The arrow glyphs 522 may provide magnitude information of blood flow based on a size of each of the arrow glyphs 522. For example, faster velocities may be shown as larger arrow glyphs 522 and slower velocities may be shown as smaller arrow glyphs 522. As shown in FIG. 5, the hexagonal packing arrangement provides vertically overlapping rows of glyphs 522 laterally offset from adjacent rows to provide a densest packing arrangement. By providing the glyphs 522 in the hexagonal packing arrangement, visualization of the blood velocity information is enhanced due to the glyphs 522 densely filling the region of interest 520 in the ultrasound image 510 to provide a heightened understanding of small flow features, such as turbulence. For example, referring to FIGS. 3 and 5, the hexagonal packing arrangement of the glyphs 522 in FIG. 5 more densely covers the region of interest 520 in the ultrasound image 510 to provide more velocity information than the glyphs 322 of FIG. 3 arranged in the grid layout in the region of interest 320 of the ultrasound image 310.

Figure 6:
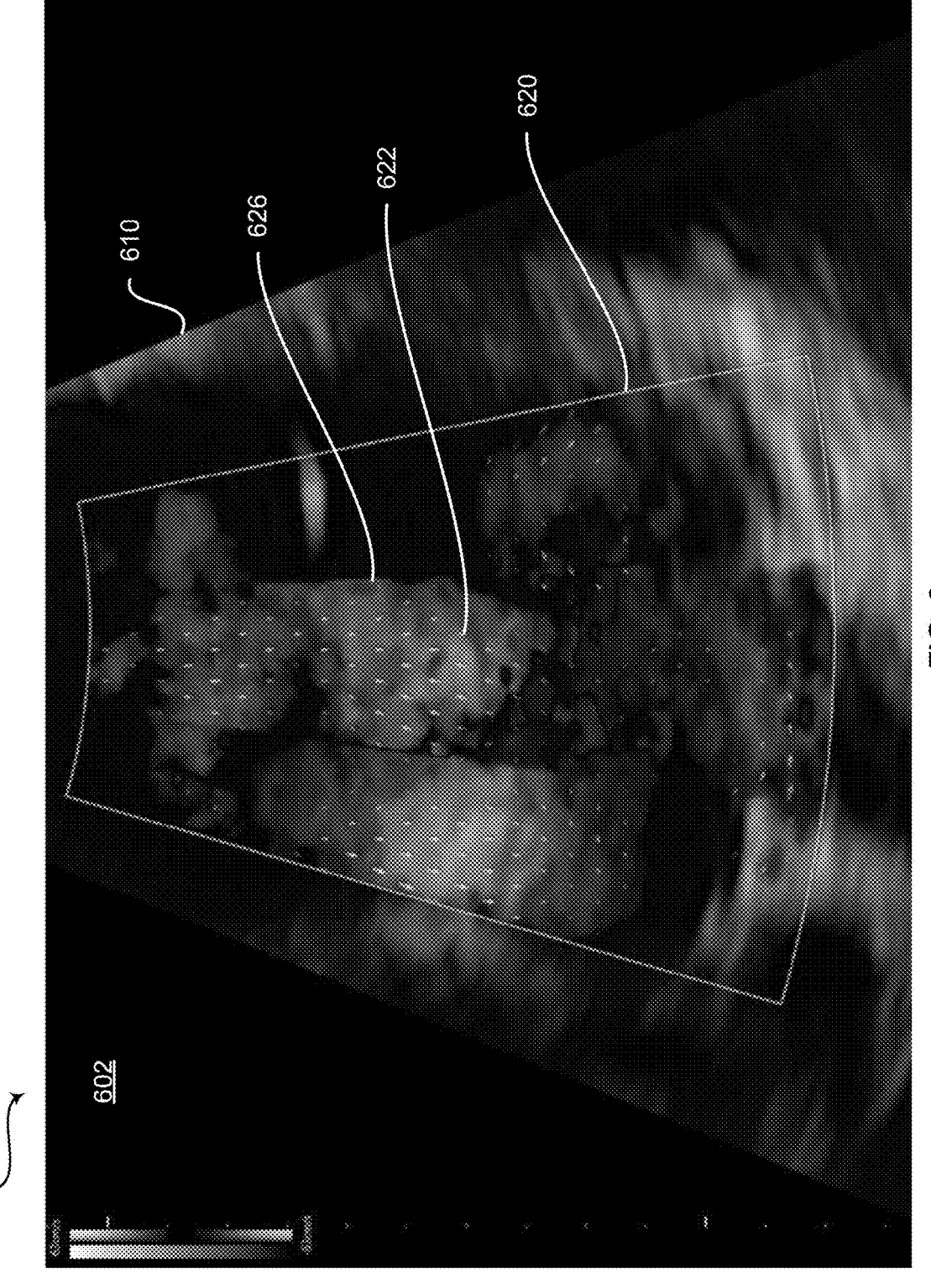
FIG. 6 is an exemplary display of linear-scaled glyphs overlaid on an ultrasound image, in accordance with various embodiments.
Figure 7:
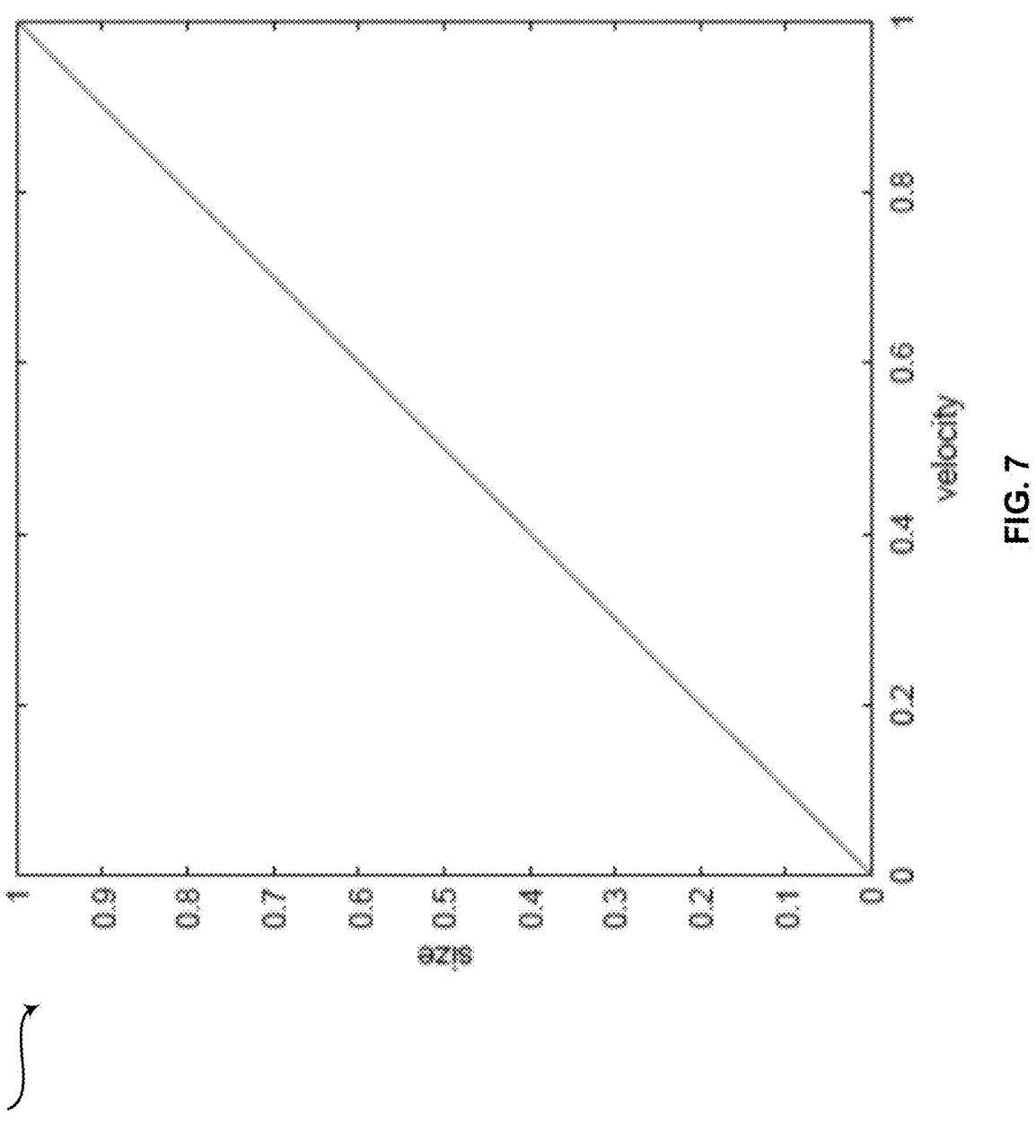
FIG. 7 is an exemplary graph of linear scaling of a size of a glyph, in accordance with various embodiments.

FIG. 6 is an exemplary display 600 of linear-scaled glyphs 622 overlaid on an ultrasound image 610, in accordance with various embodiments. Referring to FIG. 6, a display 600 includes an ultrasound image display portion 602 presenting an ultrasound image 610. The ultrasound image 610 includes a region of interest 620 that may include blood vessels having blood flow, for example. The ultrasound image 610 is overlaid with color flow Doppler information 626. The ultrasound image 610 and color flow Doppler information 626 is overlaid with linearly-scaled glyphs 622 in a hexagonal packing arrangement. The linearly-scaled glyphs 622 illustrated in FIG. 6 are arrows. The arrow glyphs 622 may provide orientation information of blood flow based on the direction the arrow glyph 622 is pointing. The arrow glyphs 622 may provide magnitude information of blood flow based on a size of each of the arrow glyphs 622. For example, faster velocities may be shown as larger arrow glyphs 622 and slower velocities may be shown as smaller arrow glyphs 622. FIG. 7 is an exemplary graph 700 of linear scaling of a size of a glyph 622, in accordance with various embodiments. Referring to FIG. 7, the graph 700 illustrates the linear sizing of the glyphs 622 of FIG. 6 based on the magnitude of the velocity. Referring again to FIG. 6, the hexagonal packing arrangement provides vertically overlapping rows of glyphs 622 laterally offset from adjacent rows to provide a densest packing arrangement. However, despite the enhancement in visualization of the blood velocity information due to the glyphs 622 densely filling the region of interest 620 in the ultrasound image 610 by providing the glyphs 622 in the hexagonal packing arrangement, some of the glyphs 622 can be difficult to visualize due to the sizing based on linearly scaling. Indeed, the glyphs 622 corresponding with slower moving flows can be particularly difficult to visualize.

Accordingly, in a preferred embodiment, the glyph visualization processor 160 may comprise suitable logic, circuitry, interfaces and/or code that may be operable to size of each of the glyphs 222, 322, 422, 522, based on a non-linear function of the velocity magnitude. In an exemplary embodiment, the non-linear function is a power function of a normalized velocity magnitude. An exponent of the power function is selected based on a desired compression of a dynamic range.

Figure 8:
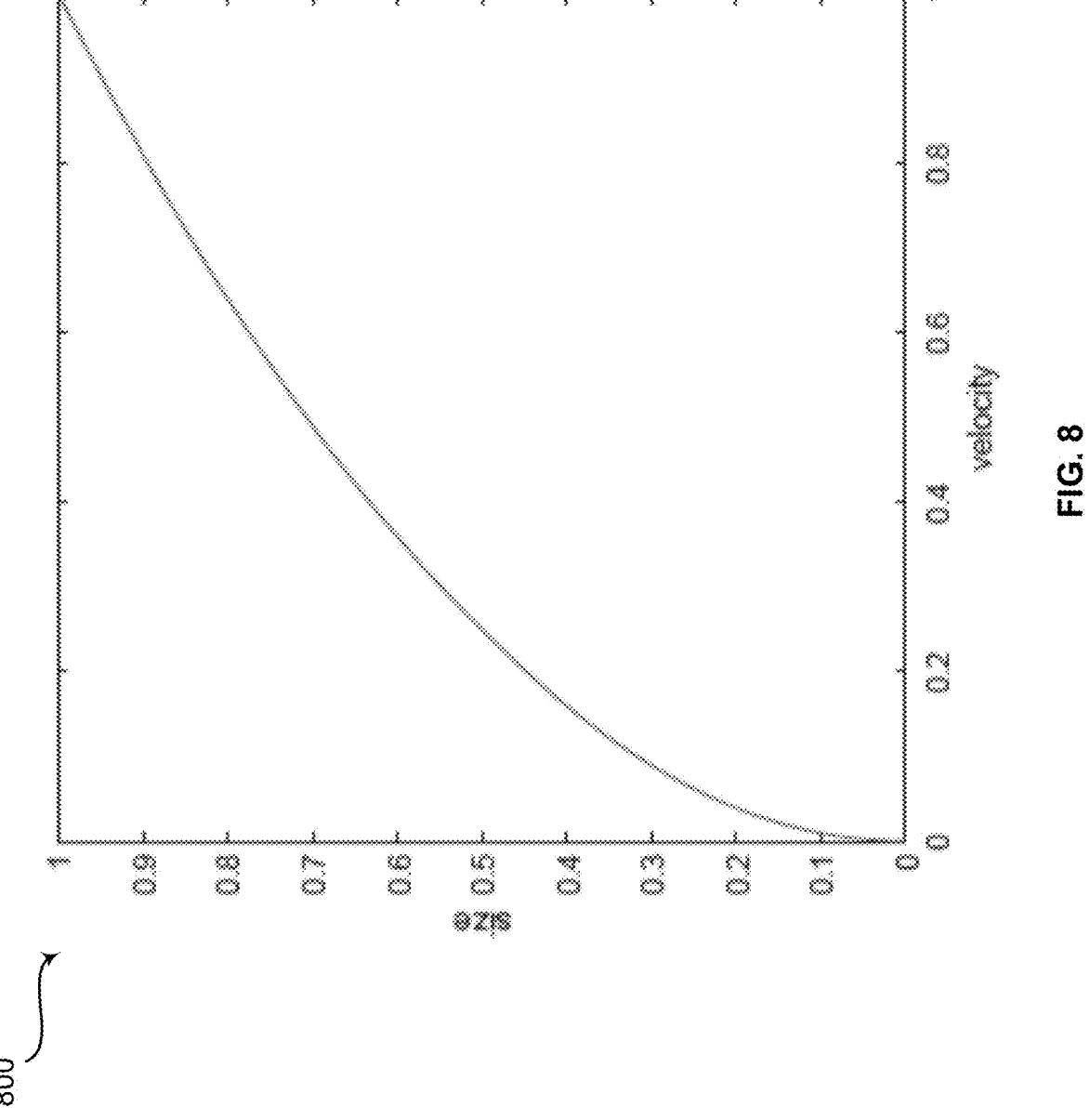
FIG. 8 is an exemplary graph of non-linear scaling of a size of a glyph, in accordance with various embodiments.

FIG. 8 is an exemplary graph 800 of non-linear scaling of a size of a glyph 222, 322, 422, 522, in accordance with various embodiments. Referring to FIG. 8, the graph 800 illustrates the non-linear sizing of the glyphs 222, 322, 422, 522 of FIGS. 2-5 based on the magnitude of the velocity. As shown in FIGS. 3 and 5, the sizing of each of the glyphs 322, 522 based on a non-linear function 800 of the velocity magnitude, instead of the linear function 700 of the velocity magnitude as shown by the glyphs 622 in FIG. 6, enhances visualization of blood flows having lower velocities by dynamically compressing the velocity magnitude using the non-linear function 800 to enlarge glyphs 322, 522 representing the lower velocity blood flows.

Figure 9:
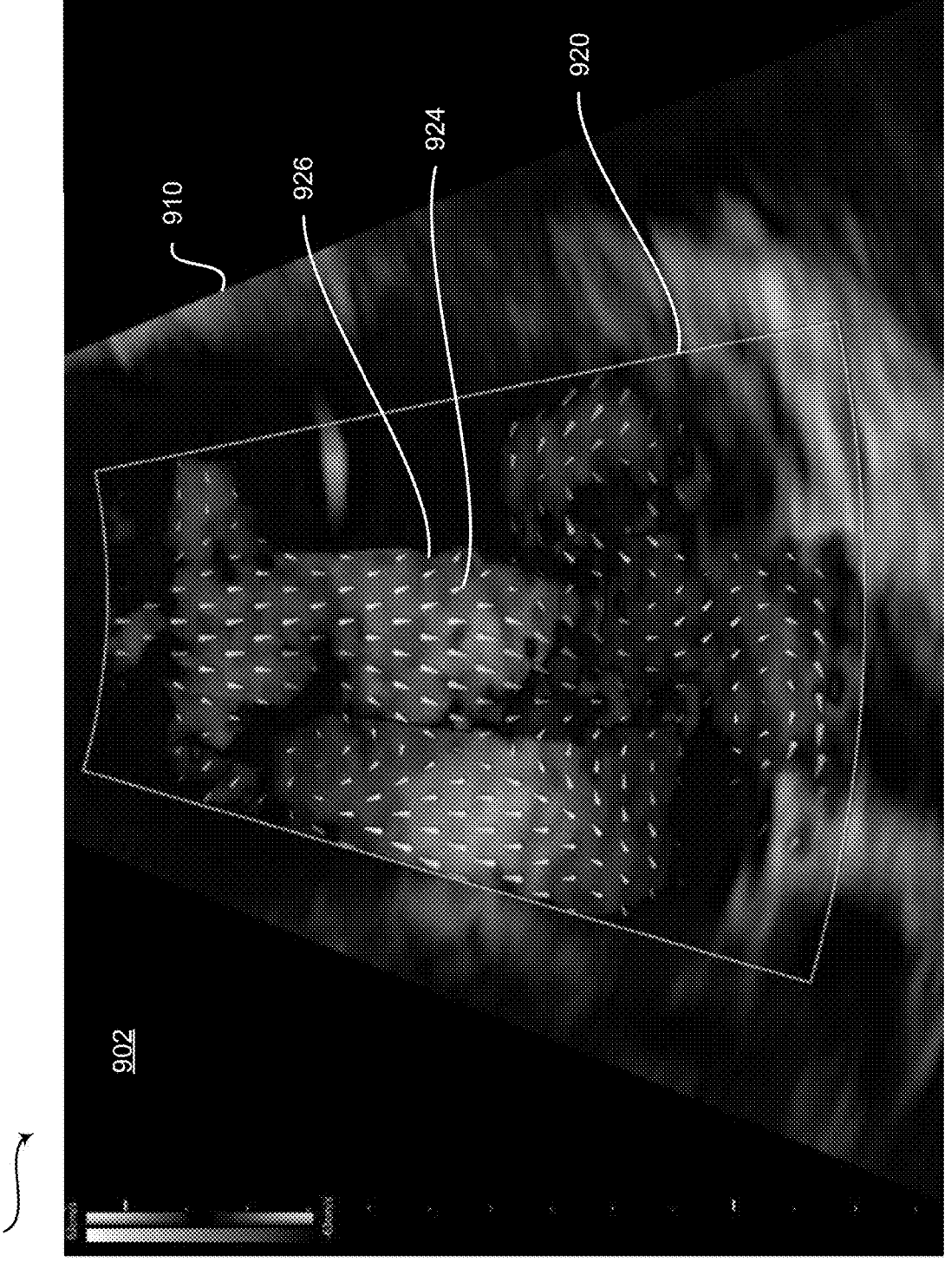
FIG. 9 is an exemplary display of drop-shaped glyphs in a hexagonal packing arrangement overlaid on an ultrasound image, in accordance with various embodiments.

Although FIGS. 2-6 illustrate glyphs 222, 322, 422, 522, 622 that are arrow-shaped, in a representative embodiment, the glyphs 222, 322, 422, 522, 622 may be any suitable shape that provides information regarding the magnitude and orientation of the blood flow. As one example, the glyphs 222, 322, 422, 522, 622 may be drop-shaped, instead of arrow-shaped. FIG. 9 is an exemplary display 900 of drop-shaped glyphs 924 in a hexagonal packing arrangement overlaid on an ultrasound image 910, in accordance with various embodiments. Referring to FIG. 9, a display 900 includes an ultrasound image display portion 902 presenting an ultrasound image 910. The ultrasound image 910 includes a region of interest 920 that may include blood vessels having blood flow, for example. The ultrasound image 910 is overlaid with color flow Doppler information 926. The ultrasound image 910 and color flow Doppler information 926 is overlaid with glyphs 924 in a hexagonal packing arrangement. The glyphs 924 illustrated in FIG. 9 are drops. The drop glyphs 924 may provide orientation information of blood flow based on the direction the thick head portion of the drop glyph 924 is pointing. The drop glyphs 924 may provide magnitude information of blood flow based on a size of each of the drop glyphs 924. For example, faster velocities may be shown as larger drop glyphs 924 and slower velocities may be shown as smaller drop glyphs 924. In a preferred embodiment, size of each of the drop glyphs 924 is based on a non-linear function 800 of the velocity magnitude. By providing the non-linear sizing of the glyphs 924, visualization of blood flows having lower velocities are enhanced by dynamically compressing the velocity magnitude using a non-linear function to enlarge glyphs 924 representing the lower velocity blood flows. As shown in FIG. 9, the hexagonal packing arrangement provides vertically overlapping rows of glyphs 924 laterally offset from adjacent rows to provide a densest packing arrangement. By providing the glyphs 924 in the hexagonal packing arrangement, visualization of the blood velocity information is enhanced due to the glyphs 924 densely filling the region of interest 920 in the ultrasound image 910 to provide a heightened understanding of small flow features, such as turbulence.

Referring again to FIG. 1, the display system 134 may be any device capable of communicating visual information to a user. For example, a display system 134 may include a liquid crystal display, a light emitting diode display, and/or any suitable display or displays. The display system 134 can be operable to present the ultrasound images 310, 510, 610, 910, region of interest 320, 520, 620, 920, color flow Doppler information 326, 526, 626, 926, glyphs 222, 322, 422, 522, 622, 924, and/or any suitable information.

The archive 138 may be one or more computer-readable memories integrated with the ultrasound system 100 and/or communicatively coupled (e.g., over a network) to the ultrasound system 100, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things. In various embodiments, the archive 138 stores instructions for generating velocity information of a region of interest 320, 520, 620, 920, superimposing color flow Doppler information 326, 526, 626, 926 on ultrasound images 310, 510, 610, 910, sizing and orienting glyphs 222, 322, 422, 522, 622, 924 based on the velocity information, and/or superimposing the glyphs 522, 622, 924 in a hexagonal packing arrangement 400 in a region of interest 520, 620, 920, for example.

Components of the ultrasound system 100 may be implemented in software, hardware, firmware, and/or the like. The various components of the ultrasound system 100 may be communicatively linked. Components of the ultrasound system 100 may be implemented separately and/or integrated in various forms. For example, the display system 134 and the user input device 130 may be integrated as a touchscreen display.

FIG. 10 is a flow chart 1000 illustrating exemplary steps 1002-1012 that may be utilized for enhancing visualization of blood flow ultrasound imaging with glyphs 222, 322, 422, 522, 622, 924 presented in a hexagonal packing arrangement 400, in accordance with various embodiments. Referring to FIG. 10, there is shown a flow chart 1000 comprising exemplary steps 1002 through 1012. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 1002, an ultrasound probe 104 of an ultrasound system 100 may transmit ultrasound beams into a region of interest 320, 520, 620, 920. For example, a transmit beamformer 110 of the ultrasound system 100 may be operable to control a transmitter 102 of the ultrasound system 100, which drives a group of transmit transducer elements 106 to emit ultrasonic transmit signals (i.e., transmit beams) into a region of interest (e.g., a heart, blood vessels, and/or the like). The transmitter 102 may be configured to receive transmit settings for driving the ultrasound probe 104 from a signal processor 132 of the ultrasound system 100. As an example, the transmitter 102 may receive transmit settings such as a transmit frequency, waveform shape, bandwidth, and/or any suitable transmit settings from the signal processor 132. The ultrasound probe 104 may be a phased array, linear array, curved array, or any suitable shape or combination of shapes. The ultrasound probe 104 may comprise an array of transducer elements, such as piezoelectric elements, micromachined elements, piezoelectric micromachined ultrasound transducers (PMUT) elements, capacitive micromachined ultrasound transducers (CMUT) elements, and/or any suitable transducer elements capable of converting control signals to acoustic energy and converting acoustic energy to ultrasound signals. The ultrasound probe 104 may comprise a group of transmit transducer elements 106 and a group of receive transducer elements 108, that normally constitute the same elements. The group of transmit transducer elements 106 may emit ultrasonic signals through oil and a probe cap and into a target. In a representative embodiment, the ultrasound probe 104 may be operable to acquire ultrasound image data covering at least a substantial portion of an anatomy, such as a heart, blood vessels, or any suitable anatomical region.

At step 1004, the ultrasound probe 104 of the ultrasound system 100 may convert received echoes to generate ultrasound signals corresponding to the ultrasound beams. For example, the ultrasound beams transmitted at step 1002 may be back-scattered from structures in the object of interest and the echoes are received by the receive transducer elements 108, which may be operable to convert the received echoes into analog signals. The analog signals may be converted to digital signals, which are demodulated to form I/Q data pairs that are representative of the corresponding echo signals. In various embodiments, the object of interest may include blood flow in a blood vessel. The I/Q data pairs (i.e., ultrasound signals) are provided to a receive beamformer 120 of the ultrasound system 100.

At step 1006, the receive beamformer 120 of the ultrasound system 100 may process the ultrasound signals to generate beamformed signals. For example, the receive beamformer 120 may be configured to perform digital beamforming processing to, for example, sum the delayed channel signals and output a beam summed signal. The resulting processed information may be the beam summed signal that is output from the receive beamformer 120 and communicated to a signal processor 132 of the ultrasound system 100.

At step 1008, the signal processor 132 of the ultrasound system 100 may process the beamformed signals to generate an ultrasound image 310, 510, 610, 910. For example, the image processor 140 of the signal processor 132 may receive the beamformed signals output from the receive beamformer 120 at step 1006. The image processor 140 may be configured to process ultrasound scan data for generating ultrasound images 310, 510, 610, 910 for presentation on a display system 134. The image processor 140 is operable to perform one or more processing operations according to a plurality of selectable ultrasound modalities on the beamformed signals. As an example, the signal processor 132 may be operable to process the beamformed signals to generate B-mode images 310, 510, 610, 910, color flow Doppler information 326, 526, 626, 926, and/or any suitable ultrasound image information. In an exemplary embodiment, the signal processor 132 may be operable to perform display processing and/or control processing, among other things. In an exemplary embodiment, the image processor 140 may be configured to superimpose color flow Doppler information 326, 526, 626, 926 on the generated B-mode images 310, 510, 610, 910. The generated B-mode images 310, 510, 610, 910 with or without the color flow Doppler information 326, 526, 626, 926 may be presented at the display system 134 and/or stored at archive 138 and/or any suitable data storage medium.

At step 1010, the signal processor 132 of the ultrasound system 100 may process the beamformed signals to generate velocity information of the region of interest 320, 520, 620, 920. For example, a blood velocity processor 150 of the signal processor 132 may be configured to analyze the beamformed signals provided by the receive beamformer 120 at step 1008 to generate velocity information of a region of interest, such as blood flow in blood vessels and/or any suitable region of interest. As an example, the blood velocity process 150 may be operable to analyze the ultrasound image data to estimate a blood velocity vector field having information regarding a magnitude and orientation of the blood flow. The blood velocity vector field may be estimated by blood speckle tracking, directional cross-correlation analysis, phase shift estimation, Doppler analysis, and/or any suitable flow vector estimation method. As an example, the blood velocity processor 150 may perform blood flow estimation over the region of interest to obtain axial and lateral velocity information of a velocity vector at any given position within the region of interest, such as using synthetic aperture imaging, a transverse oscillation approach, or any suitable approach. The blood velocity processor 150 may be configured to determine the magnitude and orientation of the blood velocity at any given point in the region of interest from the axial and lateral velocity estimates. Accordingly, the blood velocity processor 150 may be configured to generate a blood velocity vector field having information regarding a magnitude and orientation of the blood flow at any given point in the region of interest. The blood velocity vector field may be provided to the glyph visualization processor 160 and/or stored at archive 138 and/or any suitable data storage medium.

At step 1012, the signal processor 132 of the ultrasound system 100 may cause a display system 134 to present the ultrasound image overlaid with glyphs 222, 322, 422, 522, 622, 924 arranged in a hexagonal packing arrangement 400, the glyphs 222, 322, 422, 522, 622, 924 generated from the velocity information of the region of interest 320, 520, 620, 920. For example, the ultrasound image 310, 510, 610, 910 generated by the image processor 140 of the ultrasound system 100 may be presented at the display system 134. A glyph visualization processor 160 of the signal processor 132 may be configured to generate glyphs 222, 322, 422, 522, 622, 924 from the velocity information received from the blood velocity processor 150 at step 1010 and/or retrieved from the archive and/or any suitable data storage medium. The glyphs 222, 322, 422, 522, 622, 924 are graphical elements configured to provide visualization of a magnitude and orientation of blood flow at any point in the region of interest 320, 520, 620, 920. For example, the glyphs 222, 322, 422, 522, 622, 924 may be arrows 222, 322, 422, 522, 622, drops 924, and/or any suitable shape, icon, and the like capable of providing magnitude and orientation blood velocity information. As an example, an arrow glyph 222, 322, 422, 522, 622 may point in a direction corresponding with an orientation of the blood flow and may be sized to correspond with the magnitude of the blood flow. As another example, a drop glyph 924 may have a thicker head portion (opposite the thin tail portion) pointing in a direction corresponding with an orientation of the blood flow and may be sized to correspond with the magnitude of the blood flow. The glyph visualization processor 160 may be configured to superimpose glyphs arranged in a hexagonal packing arrangement 400 on the ultrasound images 310, 510, 610, 910 generated by the image processor 140. The hexagonal packing arrangement 400 is the densest packing arrangement. Accordingly, visualization of the blood velocity information is enhanced due to the glyphs 422, 522, 622, 924 in the hexagonal packing arrangement 400 densely covering a blood vessel area to provide a heightened understanding of small flow features, such as turbulence. The glyph visualization processor 160 may be configured to overlay the glyphs in the hexagonal packing arrangement 400 directly on an ultrasound image 310, 510, 610, 910 in the region of interest 320, 520, 620, 920. Alternatively, the glyph visualization processor 160 may be configured to overlay the glyphs 422, 522, 622, 924 in the hexagonal packing arrangement 400 on color flow Doppler information 326, 526, 626, 926 superimposed on the ultrasound image 310, 510, 610, 910 in the region of interest 320, 520, 620, 920. In a preferred embodiment, the glyph visualization processor 160 may be configured to size of each of the glyphs 222, 322, 422, 522, based on a non-linear function of the velocity magnitude. In an exemplary embodiment, the non-linear function is a power function of a normalized velocity magnitude. An exponent of the power function is selected based on a desired compression of a dynamic range.

Aspects of the present disclosure provide a method 1000 and system 100 for enhancing visualization of blood flow ultrasound imaging with glyphs 222, 322, 422, 522, 622, 924 presented in a hexagonal packing arrangement 400. In accordance with various embodiments, the method 1000 may comprise transmitting 1002, by an ultrasound probe 104 of an ultrasound system 100, ultrasound beams into a region of interest 320, 520, 620, 920. The method 1000 may comprise converting 1004, by the ultrasound probe 104, received echoes to generate ultrasound signals corresponding to the ultrasound beams. The method 1000 may comprise processing 1006, by a receive beamformer 120 of the ultrasound system 100, the ultrasound signals to generate beamformed signals. The method 1000 may comprise processing 1008, by at least one processor 132, 140 of the ultrasound system 100, the beamformed signals to generate an ultrasound image 310, 510, 610, 910. The method 1000 may comprise processing 1010, by the at least one processor 132, 150, the beamformed signals to generate velocity information of the region of interest 320, 520, 620, 920. The method 1000 may comprise causing 1012, by the at least one processor 132, 140, 160, a display system 134 of the ultrasound system 100 to present the ultrasound image 310, 510, 610, 910 overlaid with glyphs 222, 322, 422, 522, 622, 924 generated from the velocity information of the region of interest 320, 520, 620, 920. The glyphs 422, 522, 622, 924 are presented in a hexagonal packing arrangement 400.

In an exemplary embodiment, the region of interest 320, 520, 620, 920 comprises blood flow. In a representative embodiment, the region of interest 320, 520, 620, 920 comprises a blood vessel. In various embodiments, a size of each of the glyphs 222, 322, 422, 522, 622, 924 represent a velocity magnitude, and an orientation of each of the glyphs 222, 322, 422, 522, 622, 924 represent a flow direction. In certain embodiments, the size of each of the glyphs 222, 322, 422, 522, 924 is determined by a non-linear function 800 of the velocity magnitude. In an exemplary embodiment, the non-linear function 800 is a power function of a normalized velocity magnitude. An exponent of the power function is selected based on a desired compression of a dynamic range. In a representative embodiment, each of the glyphs 222, 322, 422, 522, 622 is an arrow shape. In various embodiments, each of the glyphs 924 is a drop shape. In certain embodiments, the method 100 comprises superimposing 1012 color flow Doppler information 326, 526, 626, 926 on the ultrasound image 310, 510, 610, 910. The glyphs 322, 522, 622, 924 are presented over the color flow Doppler information 326, 526, 626, 926.

Various embodiments provide a system 100 for enhancing visualization of blood flow ultrasound imaging with glyphs 222, 322, 422, 522, 622, 924 presented in a hexagonal packing arrangement 400. The ultrasound system 100 may comprise an ultrasound probe 104, a receive beamformer 120, at least one processor 132, 140, 150, 160, and a display system 134. The ultrasound probe 104 may be configured to transmit ultrasound beams into a region of interest 320, 520, 620, 920. The ultrasound probe 104 may be configured to convert received echoes to generate ultrasound signals corresponding to the ultrasound beams. The receive beamformer 120 may be configured to process the ultrasound signals to generate beamformed signals. The at least one processor 132, 140 may be configured to process the beamformed signals to generate an ultrasound image 310, 510, 610, 910. The at least one processor 132, 150 may be configured to process the beamformed signals to generate velocity information of the region of interest 320, 520, 620, 920. The display system 134 may be configured to present the ultrasound image 310, 510, 610, 910 overlaid with glyphs 222, 322, 422, 522, 622, 924 generated from the velocity information of the region of interest 320, 520, 620, 920. The glyphs 422, 522, 622, 924 are presented in a hexagonal packing arrangement 400.

In a representative embodiment, the region of interest 320, 520, 620, 920 comprises blood flow. In various embodiments, the region of interest 320, 520, 620, 920 is a blood vessel. In certain embodiments, a size of each of the glyphs 222, 322, 422, 522, 622, 924 represent a velocity magnitude, and an orientation of each of the glyphs 222, 322, 422, 522, 622, 924 represent a flow direction. In an exemplary embodiment, the size of each of the glyphs 222, 322, 422, 522, 924 is determined by a non-linear function 800 of the velocity magnitude. In a representative embodiment, the non-linear function 800 is a power function of a normalized velocity magnitude. An exponent of the power function is selected based on a desired compression of a dynamic range. In various embodiments, each of the glyphs 222, 322, 422, 522, 622 is an arrow shape. In certain embodiments, each of the glyphs 924 is a drop shape. In an exemplary embodiment, the at least one processor 132, 140 is configured to superimpose color flow Doppler information 326, 526, 626, 926 on the ultrasound image 310, 510, 610, 910. The glyphs 322, 522, 622, 924 are presented over the color flow Doppler information 326, 526, 626, 926.

Certain embodiments provide a system 100 for enhancing visualization of blood flow ultrasound imaging with glyphs 222, 322, 422, 522, 622, 924 presented in a hexagonal packing arrangement 400. The ultrasound system 100 may comprise an ultrasound probe 104, a receive beamformer 120, at least one processor 132, 140, 150, 160, and a display system 134. The ultrasound probe 104 may comprise a transducer 106, 108 configured to transmit ultrasound beams into a region of interest 320, 520, 620, 920 comprising blood flow and convert received echoes to generate ultrasound signals corresponding to the ultrasound beams. The transducer 106, 108 may comprise a matching layer configured to have an acoustic impedance between the blood flow of the region of interest 320, 520, 620, 920 and a material of the transducer 106, 108. The transducer 106, 108 may comprise a damping block configured to absorb ultrasound energy. The receive beamformer 120 may be configured to process the ultrasound signals to generate beamformed signals. The at least one processor 132, 140 may be configured to process the beamformed signals to generate an ultrasound image 310, 510, 610, 910. The at least one processor 132, 150 may be configured to process the beamformed signals to generate velocity information of the blood flow. The velocity information may comprise a velocity magnitude and a flow direction of the blood flow. The display system 134 may be configured to present the ultrasound image 310, 510, 610, 910 overlaid with glyphs 222, 322, 422, 522, 622, 924 generated from the velocity information of the region of interest 320, 520, 620, 920. The glyphs 422, 522, 622, 924 may be presented in a hexagonal packing arrangement 400. A size of each of the glyphs 222, 322, 422, 522, 622, 924 may represent the velocity magnitude. An orientation of each of the glyphs 222, 322, 422, 522, 622, 924 may represent the flow direction. The size of each of the glyphs 222, 322, 422, 522, 924 may be determined by a non-linear function 800 of the velocity magnitude.

In various embodiments, each of the glyphs 222, 322, 422, 522, 622, 924 is one of an arrow shape 222, 322, 422, 522, 622 and a drop shape 924.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set $\{(x), (y), (x, y)\}$. As another example, "x, y, and/or z" means any element of the seven-element set $\{(x), (y), (z), (x, y), (x, z), (y, z), (x, y, z)\}$. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" and/or "configured" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for enhancing visualization of blood flow ultrasound imaging with glyphs presented in a hexagonal packing arrangement.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method comprising:
transmitting, by an ultrasound probe of an ultrasound system, ultrasound beams into a region of interest;
converting, by the ultrasound probe, received echoes to generate ultrasound signals corresponding to the ultrasound beams;
processing, by a receive beamformer of the ultrasound system, the ultrasound signals to generate beamformed signals;
processing, by at least one processor of the ultrasound system, the beamformed signals to generate an ultrasound image;
processing, by the at least one processor, the beamformed signals to generate velocity information of the region of interest; and
causing, by the at least one processor, a display system of the ultrasound system to present the ultrasound image overlaid with glyphs generated from the velocity information of the region of interest, wherein the glyphs are presented in a hexagonal packing arrangement, wherein:
a size of each of the glyphs represent a velocity magnitude,
an orientation of each of the glyphs represent a flow direction, and
the size of each of the glyphs is determined by a non-linear function of the velocity magnitude.

2. The method of claim 1, wherein the region of interest comprises blood flow.

3. The method of claim 2, wherein the region of interest comprises a blood vessel.

4. The method of claim 1, wherein the non-linear function is a power function of a normalized velocity magnitude, wherein an exponent of the power function is selected based on a desired compression of a dynamic range.

5. The method of claim 1, wherein each of the glyphs is an arrow shape.

6. The method of claim 1, wherein each of the glyphs is a drop shape.

7. The method of claim 1, comprising superimposing color flow Doppler information on the ultrasound image, wherein the glyphs are presented over the color flow Doppler information.

8. An ultrasound system comprising:
an ultrasound probe configured to:
transmit ultrasound beams into a region of interest; and
convert received echoes to generate ultrasound signals corresponding to the ultrasound beams;
a receive beamformer configured to process the ultrasound signals to generate beamformed signals;
at least one processor configured to:
process the beamformed signals to generate an ultrasound image; and
process the beamformed signals to generate velocity information of the region of interest; and
a display system configured to present the ultrasound image overlaid with glyphs generated from the velocity information of the region of interest, wherein the glyphs are presented in a hexagonal packing arrangement,
wherein:
a size of each of the glyphs represent a velocity magnitude,
an orientation of each of the glyphs represent a flow direction, and
the size of each of the glyphs is determined by a non-linear function of the velocity magnitude.

9. The ultrasound system of claim 8, wherein the region of interest comprises blood flow.

10. The ultrasound system of claim 9, wherein the region of interest is a blood vessel.

11. The ultrasound system of claim 8, wherein the non-linear function is a power function of a normalized velocity magnitude, wherein an exponent of the power function is selected based on a desired compression of a dynamic range.

12. The ultrasound system of claim 8, wherein each of the glyphs is an arrow shape.

13. The ultrasound system of claim 8, wherein each of the glyphs is a drop shape.

14. The ultrasound system of claim 8, wherein the at least one processor is configured to superimpose color flow Doppler information on the ultrasound image, wherein the glyphs are presented over the color flow Doppler information.

15. An ultrasound system comprising:
an ultrasound probe comprising a transducer configured to transmit ultrasound beams into a region of interest comprising blood flow and convert received echoes to generate ultrasound signals corresponding to the ultrasound beams, wherein the transducer comprises:
a matching layer configured to have an acoustic impedance between the blood flow of the region of interest and a material of the transducer; and
a damping block configured to absorb ultrasound energy;

a receive beamformer configured to process the ultrasound signals to generate beamformed signals;

at least one processor configured to:

process the beamformed signals to generate an ultrasound image; and process the beamformed signals to generate velocity information of the blood flow, wherein the velocity information comprises a velocity magnitude and a flow direction of the blood flow; and a display system configured to present the ultrasound image overlaid with glyphs generated from the velocity information of the region of interest, wherein:

the glyphs are presented in a hexagonal packing arrangement, a size of each of the glyphs represent the velocity magnitude, an orientation of each of the glyphs represent the flow direction, and the size of each of the glyphs is determined by a non-linear function of the velocity magnitude.

16. The ultrasound system of claim 15, wherein each of the glyphs is one of an arrow shape and a drop shape.

\* \* \* \* \*